United States Patent [19]

Sluyter

[11] Patent Number: 4,600,940

[45] Date of Patent: Jul. 15, 1986

[54] VIDEO CAMERA FOR USE WITH AN ENDOSCOPE AND METHOD FOR MAKING SAME

[75] Inventor: Erik Sluyter, Santa Barbara, Calif.

[73] Assignee: Circon Corporation, Santa Barbara, Calif.

[21] Appl. No.: 578,108

[22] Filed: Feb. 7, 1984

[51] Int. Cl.⁴ .............................................. H04N 7/18
[52] U.S. Cl. ...................................... 358/98; 358/229
[58] Field of Search ................ 358/98, 209, 901, 213, 358/229; 128/4-11

[56] References Cited

U.S. PATENT DOCUMENTS

| | | | |
|---|---|---|---|
| 3,499,107 | 3/1970 | Sheldon | 358/209 |
| 3,520,587 | 7/1970 | Tasaki et al. | 358/901 X |
| 3,809,908 | 5/1974 | Clanton | 358/901 X |
| 4,281,910 | 8/1981 | Takayama | 128/4 X |
| 4,344,092 | 8/1982 | Miller | 358/98 X |
| 4,414,608 | 11/1983 | Furihata | 128/4 X |
| 4,473,841 | 9/1984 | Murakoshi et al. | 358/901 X |
| 4,491,865 | 1/1985 | Danna et al. | 358/98 |

FOREIGN PATENT DOCUMENTS

| | | | |
|---|---|---|---|
| 0105731 | 7/1982 | Japan | 358/98 |
| 0108839 | 7/1982 | Japan | 358/98 |
| 0176027 | 10/1982 | Japan | 358/98 |

Primary Examiner—James J. Groody
Assistant Examiner—Victor R. Kostak
Attorney, Agent, or Firm—Daniel J. Meaney, Jr.

[57] ABSTRACT

A video camera for use in medical surgical procedure in conjunction with an endoscope is shown. The video camera includes an optical system for receiving and optically processing an optical image from an endoscope. A solid-state sensor-converter is operatively positioned to receive the optical image after it is passed through the optical system and for converts the optical image into an unprocessed video signal. A video processing circuit is located adjacent the optical system and is electronically connected to receive the output of the sensor convertor. The video processing circuit is mounted around the optical system and transmits preprocessed output signals as an output from the video electronic processing circuit to a remote location and to a video output circuit. A soakable enclosure surrounds the optical system, the solid-state sensor converter and the video electronic processing circuit and includes a sealing member for maintaining the same in operative relationship. An adapter permits the input of the optical image into the optical system and electrical conductors are used for transmission of the preprocessed output signals therefrom.

9 Claims, 10 Drawing Figures

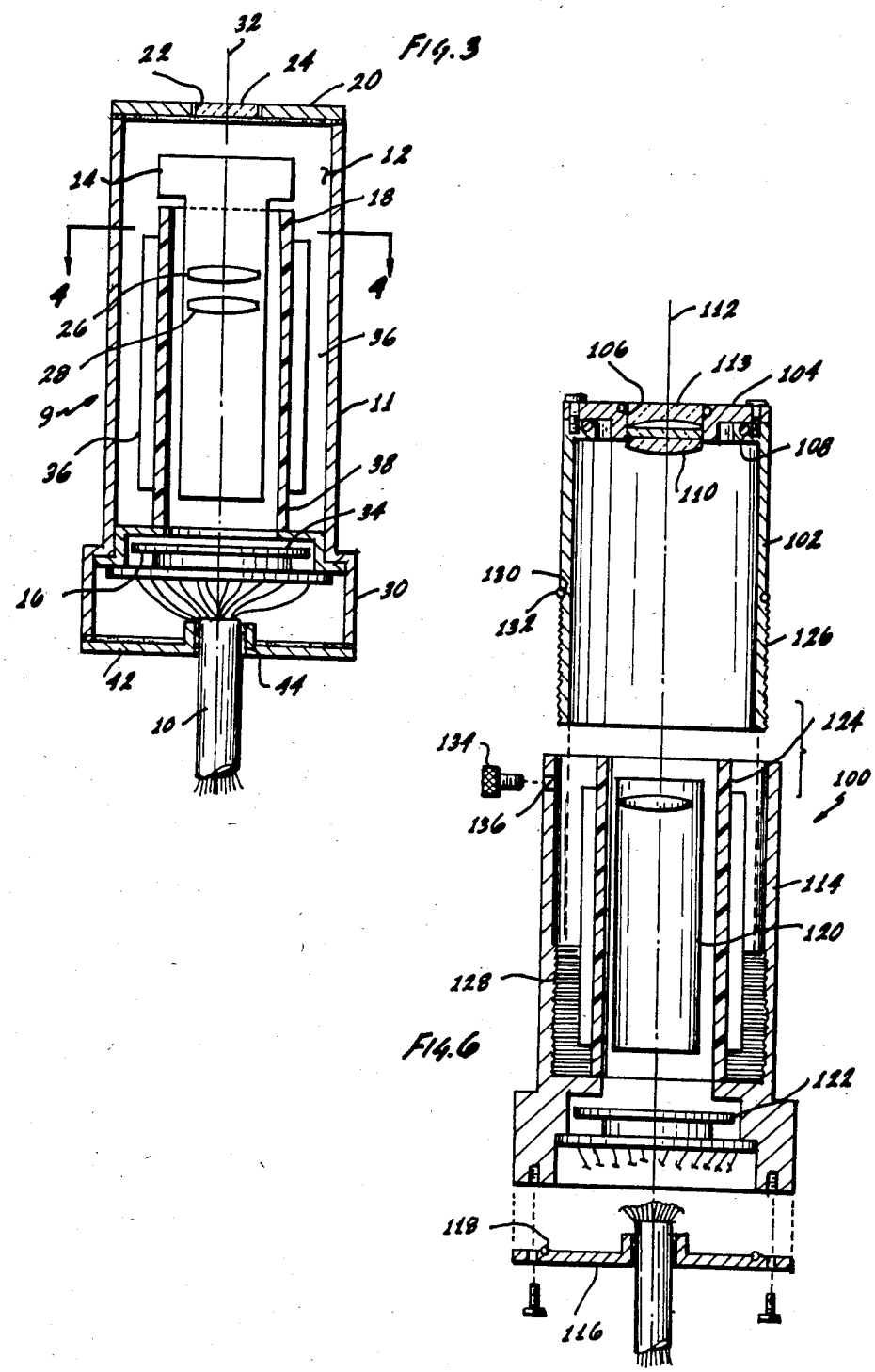

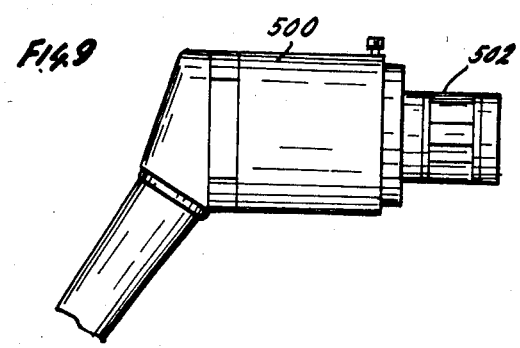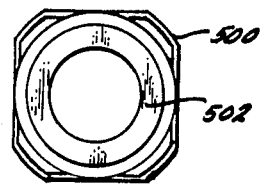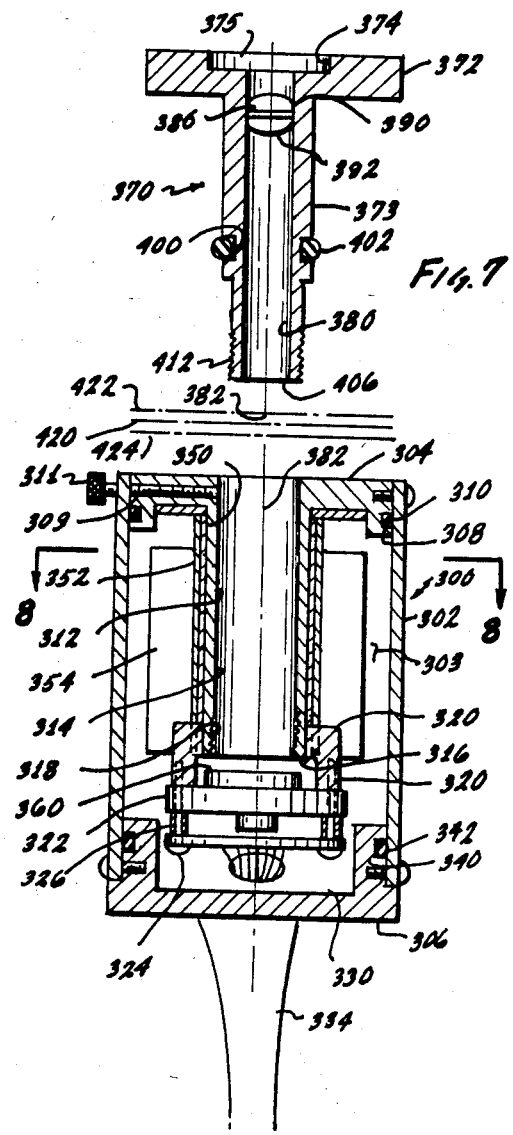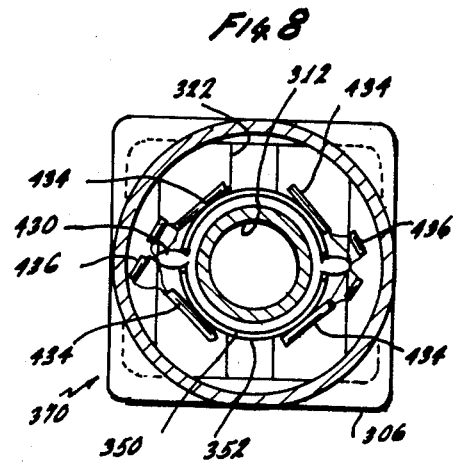

VIDEO CAMERA FOR USE WITH AN ENDOSCOPE AND METHOD FOR MAKING SAME

BACKGROUND OF THE INVENTION

This invention relates to video cameras for use in conjunction with endoscopes in medical and surgical applications. In particular, the invention relates to video cameras which are or may be attached to the end of the endoscope operated by medical personnel where an image from a selected area inside a patient's body cavity is produced external to the endoscope.

Endoscopes have established a wide variety of utility in the medical and surgical fields for viewing inside the human body. For example, endoscopes are useful in the surgical specialties of arthroscopy, bronchoscopy, colonoscopy, cystoscopy, gastroscopy, laparoscopy, laryngoscopy, sigmoidoscopy, microsurgery, neurosurgery, colposcopy, ophthalmology/corneal surgery with microscope, ophthalmology/vitreous surgery with microscope, and ophthalmology/indirect examination and general surgery. In typical applications, the forward end of an endoscope is placed in the body cavity where viewing is desired. An illumination means is provided either as part of the endoscope or by a separate means. The endoscope end senses imagery in the cavity and transmits that imagery, typically by means of a fiber optic bundle to an output means at the end of the endoscope outside the body. The light signals delivered at the output end of the endoscope are then employed in a variety of ways, such as by direct viewing or through beam splitting by both direct viewing and to a camera for television viewing or by television viewing alone. Where it is desired to televise the endoscopy, the features desired in the camera are complex due to the large performance differences in different types of endoscopes, the reduced light transmission of endoscopes with age, the wide variety of light sources, the variation of type of cavity into which the endoscope may be inserted, and the need for ease of handling and light weight to facilitate use. Light transmission is a key variable among endoscopes. The type and size of endoscope greatly affects the amount of light transmitted from a subject to the television camera. For example, larger glass fiber bundles yield more light, hence, a brighter image which is easier to televise. The outside diameter of endoscopes of the same type may be an indication of the size of the glass fiber bundle. In general, shorter and larger diameter endoscopes transfer more light than longer or smaller diameter instruments. Operating endoscopes usually have smaller light transmission bundles than diagnostic types to permit channels for instruments, air, and/or water. Thus, it is usually easier to televise imagery from diagnostic endoscopes than from operating endoscopes, given the same medical circumstances.

Light transmission of fiber optic bundles in an endoscope declines with age. Also, usage tends to break individual fibers, reducing the amount of light transmitted. Exposure to heat gradually yellows the fibers, degrading light transmission and distorting the color. High usage endoscopes, therefore, requires brighter light sources or increased camera sensitivity for satisfactory television viewing. For maximum light transmission, an endoscope should have clean optics and light channels. It is important that the cameralight-source combination used in endoscopy provides sufficient sensitivity and intensity to produce a satisfactory color television image. Manufacturers of endoscopes offer several light sources having a great range of intensity. In selecting a light source, it is important to consider the viewing media in that television viewing requires a more brightly lit subject than direct ocular viewing. A common endoscopy problem is the dramatic reduction in image intensity resulting when the endoscope moves from a small body passage into a much larger cavity. In a small passage, there may be more than adequate illumination for a distance from the endoscope tip to the subject, for example, up to 20 millimeters. However, when the endoscope enters a larger cavity, the subject distance may increase, for example, up to 100 millimeters or greater. At 100 millimeters, the light on the subject is reduced by the inverse square of the subject distance to about 4 percent of the light available at 20 millimeters. In addition, the relative angle of the tissue to be viewed may change, altering the reflectivity of the surface. Further, small diameter cavities often act as a reflector directing light forward toward the viewing area.

Typically, for viewing video endoscopy, a 12-inch television monitor is satisfactory. The size of the image on a particular monitor is determined by the magnification of the endoscope. Image size as a percentage of screen height is important from the standpoint of brightness and resolution. As the image is enlarged to full screen height, the image resolution will increase because more video scanning lines are utilized. However, image brightness decreases as a function of the square of image size. With constant illumination and no light change, a 40 percent larger image will be 50 percent less bright.

A number of video cameras for endoscopy have been available. For example, a color television endoscope camera is made by Circon Corporation, Model MV 9330/35. This camera weighs 6 ounces and employs a pick up tube two-thirds of an inch in length. Also, Circon Corporation has had available various optical accessories, including couplers, eye piece adapters, and beam splitters. The resulting video system is sufficiently small and light that it can be mounted directly on any rigid or flexible endoscope. Since the color television camera receives a direct image from the endoscope, its image brightness, color fidelity, and resolution are superior to larger size cameras, which must be connected to an endoscope through articulated lenses or fiber optic links. Moreover, such links can cause image rotation and waste valuable image intensity, thereby interfering with the endoscopy process. For the interface of a video camera to an endoscope, an optical coupler is normally employed. The coupler connects the camera directly to the endoscope. Thus, all the available light goes directly into the camera, permitting the brightest possible television image. However, it is also possible to interpose a beam splitter between the endoscope and the camera optics for direct viewing as well as video monitor viewing. Furthermore, it is common to apply an adapter ring to the endoscope for easily removing the video camera or the beam splitter when used, thus providing direct viewing to the endoscope.

All video cameras compensate for some range of light level. However, that range is frequently exceeded when viewing tissue at varying distances from the distal tip of the endoscope and varies as a function cavity size. The result is washed out or darkened images. It can be seen that size, weight, and sensitivity are important features of video cameras for use in conjunction with endoscopes. The aforementioned Circon Corporation Model MV 9330/035 camera, for example, is 1½ inches diameter by 5½ inches long and weighs six ounces. Another camera, also made by Circon Corporation, is Model MV 9320/25, which has particularly low light level sensivity, being about 10 times more light sensitive than any other color television endoscope camera. This camera is 1½ inches in diameter by 5½ inches long and weighs also six ounces. Its unique light sensitivity is particularly advantageous in televising very difficult microsurgery. The above-described devices are employed first by use of an adapter fixed to the end of the endoscope which receives an optical coupler having therein an optical system for passing the image to the camera. At the end of the coupler, a camera is attached. The coupler-and-camera combination receives optical imagery from the output end of the endoscope and converts it to preprocessed color video signals which are then transmitted for processing and projection on a color television monitor.

Although a high degree of miniaturization has been made possible by advances in the manufacture of electronic components and circuitry, and substantial light weight has been made possible similarly by advances in materials sciences, it is, nevertheless, very desirable to further reduce the size and weight of the entire endoscope video system, particularly that portion of the system which is directly attached to the end of the endoscope and which must be handled by medical personnel.

SUMMARY OF THE INVENTION

The method of the present invention for manufacturing a video camera for use in conjunction with an endoscope provides for forming a hollow body and enclosing within the body an optical system for receiving and transmitting optical imagery from an endoscope and placing around the outside of the optical system, but within the same body, electronic circuitry for preprocessing video signals received from a sensor-converter located within the body and behind the optical system. The apparatus of the invention is that resulting from the foregoing method.

BRIEF DESCRIPTION OF THE DRAWINGS

The foregoing and other advantages of this invention will become apparent from the following description of the preferred embodiments when considered together with the accompanying drawings, which include the following figures:

FIG. 3 is a lengthwise section view through the optical axis of the optical system, along line 3—3 of FIG. 4;

FIG. 6 is a sectional view of an alternative embodiment of the invention.

FIG. 7 is a lengthwise sectional view of an alternate embodiment of the invention.

FIG. 8 is a sectional view of the embodiment of FIG. 7.

FIG. 9 and FIG. 10 illustrate yet another embodiment for practicing the invention.

DETAILED DESCRIPTION OF THE PREFERRED EMBODIMENT

Figure 1:
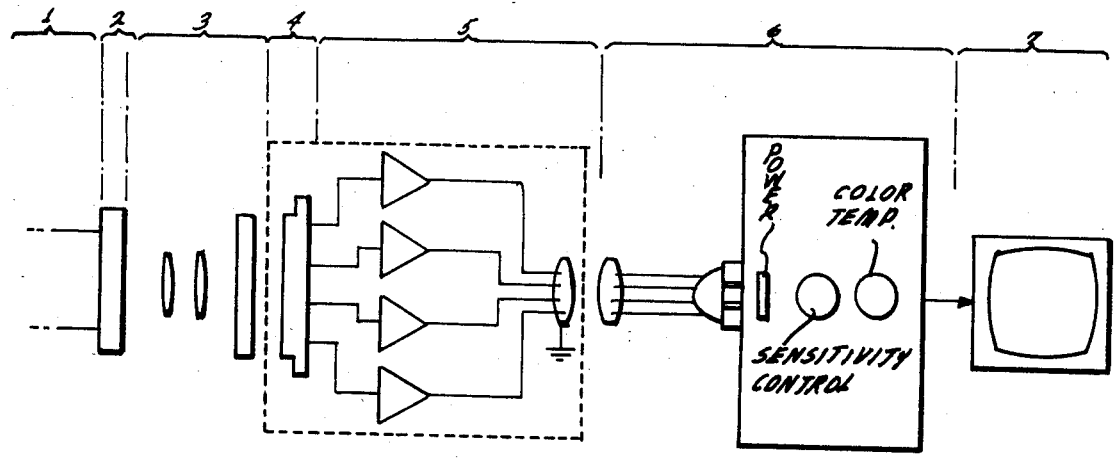
FIG. 1 is a diagram of a video system which employs the invention.

FIG. 1 shows a general diagram of an endoscope video system comprising the output end of an endoscope 1, an adapter 2 for connecting the endoscope 1 to an optical system 3, a solid state sensor-converter 4 which receives light from the optical system 3 and converts it in a known manner to electronic signals capable of being further processed for video display, the sensor-converter 4 being connected to driver-preamplifiers of the preprocessing electronics 5, whose output signals are transmitted to the processing electronics 6, and finally the video signals are transmitted to the video monitor 7. With this general description of an endoscope video system in mind, the subject of the present invention can be fully described.

Figure 2:
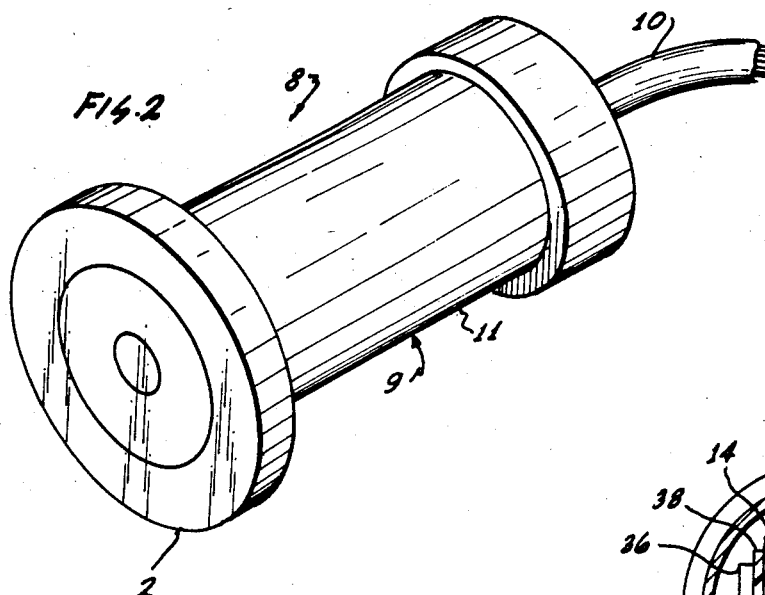
FIG. 2 is a perspective view of the outside of the camera of the present invention along with an adapter for facilitating attachment to an endoscope.

In FIG. 2 there is shown an external view of the camera 8 of the present invention comprising a body 9 and, attached to it, an adapter 2 for attaching the camera 8 to an endoscope. The adapter 2 is of a conventional known design. Also, a cable 10 is shown extending from the most rearward portion of the body 9 and will normally extend to a video processing system for processing and projecting video signals onto a video monitor.

As shown in FIGS. 2 and 3, the endoscope video camera of the present invention is made up of the body 9 shown generally at 9, which is adapted for containing and having mounted therein the various components of the camera. In particular, the body 9 has a main cylinder portion 11 which defines a cavity 12, in which are mounted the three subsystems of the camera, namely, the optical lens system 14, the sensor-converter 16, and the preprocessing electronics 18.

The body 9 has a forward end 20 which has an aperture 22. The aperture 22 is sealed and covered by a window 24. The optical lens system 14 is aligned behind the aperture 22 and is illustrated by lenses 26 and 28, defining an optical axis 32. Although the window 24 and simple lenses 26 and 28 are here illustrated, a more complex system, including one in which the window 24 would be used as a lens, could be employed in a manner known to those skilled in the art.

The sensor-converter 16 has a receiving surface 34 which is a self-scanning solid state imaging device, such as a charge coupled device (CCD) or a Mos device located in the image plane of the lens system 14, and mounted in a slightly enlarged, cylindrical portion 30, of the body 9, rearward of the main cylinder portion 11. The specific construction and operation of such a Mos imager is known to those skilled in the art and exemplified by the Hitachi Model HE 98221. The preprocessing electronics 18 are operatively connected, in a known manner, to the sensor-converter 16.

The preprocessing electronics 18 include four integrated circuit packages 36, one to process each of the color signals—yellow, white, green, and cyan. Such integrated circuits are well known in the art. The integrated circuit packages 36 are mounted on printed wiring substrates 38 which are arranged around the outside of the lens system 14, extending inside the main cylinder portion 11 and mounted to the body 9. Thus, the lens system 14 and the preprocessing electronics 18 effectively occupy the same space within the body 9. This results in considerable savings and improvement over prior devices in both size and weight. The printed wiring substrate 38 is made in a known manner according to the required circuit from flexible, plastic material. The printed wiring substrate 38 may be configured in a number of variations in order to extend around the lens system 14.

Figure 4:
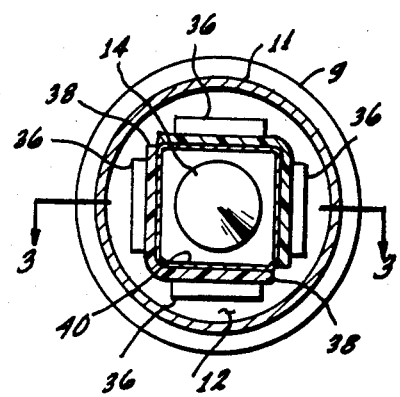
FIG. 4 is a sectional view through line 4—4 of FIG. 3.

In FIG. 4, two separate substrates, which could be relatively rigid with a flexed or bent corner portion, are shown. Also, the substrate could be one piece of flexible-type circuit positioned around the lens system with flat areas upon which the integrated circuit packages 36 are mounted. In order to maintain the printed wiring substrate 38 and its accompanying integrated circuit (IC) packages 36 in place and separated from the optical lens system 14, it is desirable that a substructure, such as illustrated at 40, be placed beneath the substrate. As an example of such substructure 40, material known as "fishpaper" folded into a generally square shape may be employed. Further, the printed wiring substrate 38 rests inside the body 9 upon a shoulder inside the cavity 12 where additional mounting means may be employed to retain the circuit in a fixed position.

Rear enclosure 42 closes the rear of the body 9. Rear enclosure 42 has an aperture 44 through which cable 10 sealably passes. The cable 10 carries wires operatively attached to the electronic means within the body carrying video signals to a color video processor at a remote location and thereafter to a video monitor and includes means for providing power to operate the internal electronics. A sealing means, illustrated in FIG. 6 as a circular ring seal, such as an O-ring, seals the rear enclosure 42, where it attaches to the cylindrical portion 11. Also, the forward end 20 may be formed as a separate sealable cover, similarly employing a sealing means as illustrated in FIG. 6, by an O-ring seal. Use of a separate sealably attachable forward end 20 and rear enclosure 42 is preferred for simplicity of manufacture of the body 9. It is an important feature of the camera that the optics and electronics are carried in a single-body portion in a very compact manner so that the optics and preprocessing electronics reside in the same part of the body, effecting dual use of that part of the body and eliminating the need for separate parts. Also, this combined optical and electronic camera structure is easily sealable to be soakable in disinfectant for medical purposes, which is accomplished by the sealable features of both the rear enclosure 42 and the forward end 20 which is more fully described with reference to FIG. 6.

Figure 5:
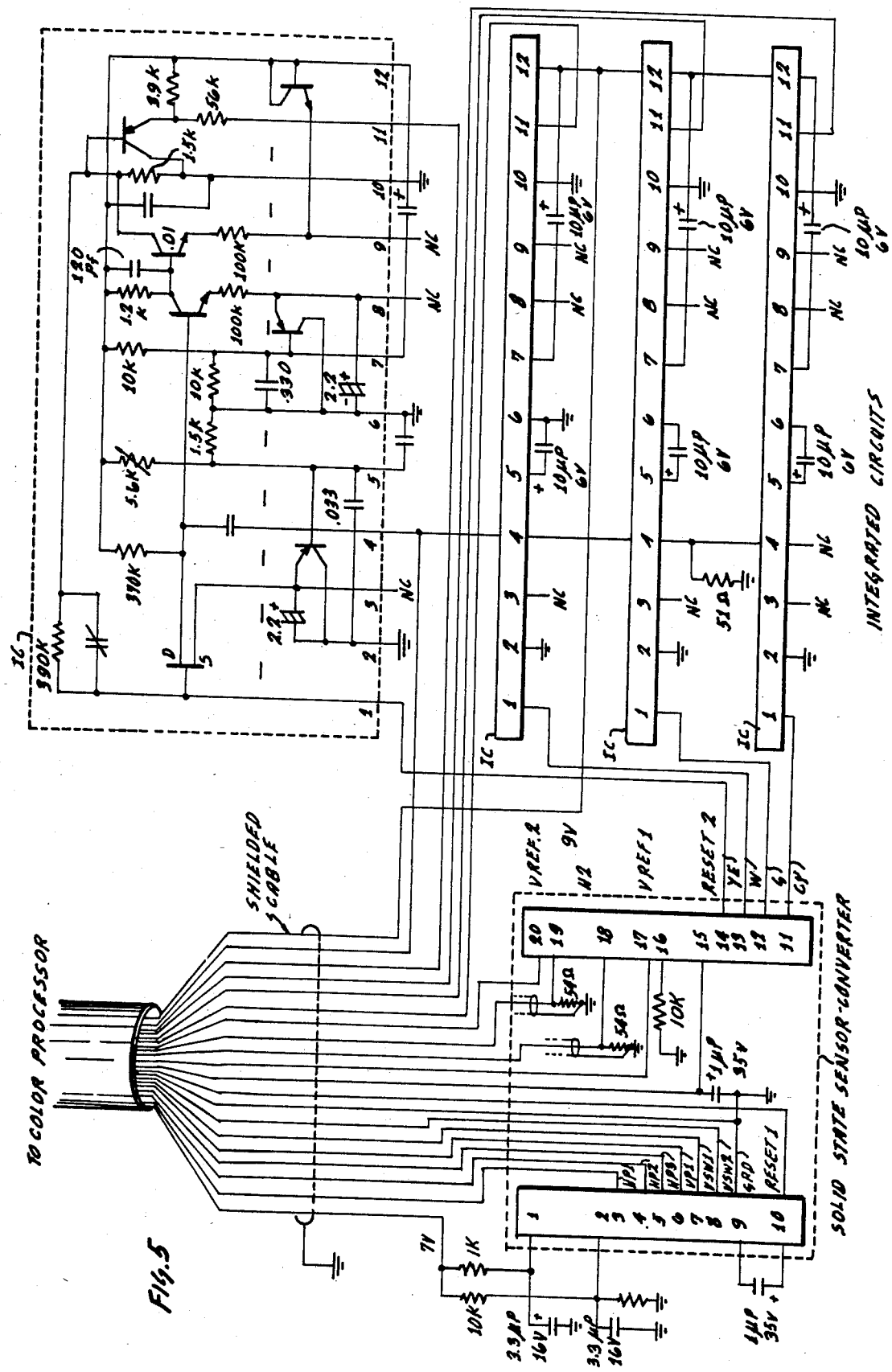
FIG. 5 is the electronic circuit of the camera.

In FIG. 5, the electronic circuit of the camera is converter 16 and the integrated circuits 36. Where component values are shown in FIG. 5, capacitor values are in microfarads and resisters in thousand ohms, except as otherwise noted. The circuit of the four integrated circuits 36 are the same, one of them being shown in detail.

In use, the camera of the present invention has placed on its front end an adapter 2, of known design, as shown in FIG. 1, which is then attached in a known manner to the receiving end of an endoscope or, alternatively, to the receiving end of a beam splitter, which is attached to the receiving end of the endoscope.

The manner of operation of the present camera is well known to those skilled in the art and, therefore, need not be described herein in detail. In general, optical imagery transmitted through the endoscope to its output end passes through the window 24 and is transmitted through the optical lens system 14 to impinge upon the receiving CCD grid pattern of the sensor-converter 16. Electrical signals from the sensor-converter 16 are transmitted through appropriate wiring to the preprocessing electronics 18 and thereafter through interconnected wiring to the cable 10 to connect to a color video system in a remote location. The sensor-converter 16 is activated and controlled by means of interconnections through the cable 10 and from the preprocessing electronics 18.

An alternative embodiment of the invention is shown in FIG. 6, which includes all the advantages of the invention as previously described but has the additional feature that the optical system is focusable. In this embodiment, the body 100 is formed of two parts. The first body portion 102 is a cylinder which retains a forward portion 104, which has in it an optical aperture 106. The forward portion 104 is sealably attached to the first body portion 102 by means of seal 108. A forward portion of the optical system 110 is attached to the first body portion 102, aligned with the optical aperture 106 defining an optical axis 112. As previously mentioned, the aperture 106 is covered by a window 113, which could also be part of the optical system. A rearward second body portion 114 is also in the form of a cylinder and retains the rear closure 116, sealed by means of the seal 118. The first body portion 102 is telescoped inside the second body portion 114.

Mounted inside the second body portion 114 is a rear portion 120 of the optical system. The sensor-converter 122 and the preprocessing electronics 124 are shown mounted in and are connected in the second body portion 114 in a manner similar to that hereinbefore described. On the outer periphery of the cylindrical first body portion 102 is a thread 126, and on the inner periphery of the second body portion 114 is a thread 128, the threads 126 and 128 being interengageable so that relative rotation of the first body portion 102 and the second body portion 114 will cause relative movement of the forward portion 110 and the rearward portion 120 of the optical system to accomplish focusing.

The telescoped cylindrical parts of the body portions 102 and 114 should be sized for close but freely movable fit. For sealing, a groove 130, in the first body portion 102 contains an O-ring seal 132. A set screw 134 in a threaded hole 136 acts to retain the two body portions in position to maintain the focus of the optical system.

This alternative embodiment operates in the same manner as previously explained. However, it provides the additional feature of focusing the image at the image plane. The sensing base of the sensor-converter 122 is preferably located at the image plane.

FIG. 7 illustrates an alternative embodiment of an endoscope camera using the teachings of this invention. The body is shown generally as 300. The cylindrical body 302 has a cavity 303 which is adapted to receive a top member 304 and a bottom member 306. Top member 304 includes an annular slot 308 which is adapted to sealingly receive an O-ring 310. The top member 304 includes a thin-walled, elongated, cylindrically shaped, tubular member 312 which extends a predetermined length into the cavity 303. The top member 304 includes a threaded hole 309 for accepting extended locking member 311.

The interior sidewall 314 of the tubular member 312 has located near its termination in the cavity at 316 internal threads 318. At its termination in the cavity, there is located on the exterior sidewall of the tubular member 312 a pair of opposed elongated finger-like supports 320 for spacing the end 316 from a solid-state imaging device 322 which is attached by fasteners 324 through spacer 326 to the supports 320.

The bottom member 306 includes a recessed area 330 which accommodates the electrical conductors 332 from cable 334. The bottom member 306 likewise includes an annular slot 340 for receiving a sealing O-ring 342.

In addition, an assembly formed of two concentric cylindershaped members 350 and 352 which are formed of copper and Delrin, respectively, installed concentrically on tubular member 312 are part of a video processing means and are utilized for supporting the video processing electronics shown generally as 354. The details of the assembly comprising the video processing means is shown in FIG. 8.

As is shown in FIG. 7, the central area of the tubular member 312 provides an optical path for an optical image which is to be focused on the sensing face 360 of the solid-state imaging device 322. In the preferred embodiment, the solid-state imaging device 323 is an MOS sensor.

An adapter member, shown generally by 370, includes a circular top member 372, having a recess 373 to define an optical aperture. A tubular, elongated, thin-walled support member 370 having an elongated central area 380 communicates with optical aperture 374, to define an optical path which extends along the longitudinal axis of the circular top member 372 illustrated by dashed line 382. A transparent element 375 is fitted in recess 374.

An optical system 386, formed of achromatic lens element 390 and 392, is adapted to pass an optical image from an endoscope (not shown) which enters through window 374, along the optical path and defining an optical axis 382.

The tubular member 370 includes an annular slot 400 which receives an O-ring 402 which is adapted to sealingly, slidingly move on the interior wall 314 of the elongated tubular member 312.

The interior end 406 of elongated member 370 has threads 412 formed on the exterior wall of elongated member 378. The threads 412 are adapted to coact with threads 318 when the adapter 370 is inserted into the body 300.

The threads 412 and 318 cooperate and coact with each other to enable relative rotatable movement between adapter 370 and body 300 such that the focal plane of the optical system 386 can be adjusted as illustrated diagramatically by focal plane lines 420, 422 and 424, within the body 300. In use, the adapter 370 is rotatingly mounted within the body 300 and rotatable therewith to focus the optical image, located at the focal plane, onto the imaging surface 360 of the solid-state imaging device 322.

FIG. 8 shows in section that the body 302 is cylindrical in shape with the bottom member 306 being rectangular in shape.

The video processing means include the copper cylindrically shaped member 350 and a Delrin cylindrically shaped member 352, concentrically mounted thereon and concentrically mounted on the tubular member 312 to form an inner copper conductive support member and Delrin insulating member. The Delrin insulating member has a plurality of apertures or slots formed therein through which elongated conductive terminals 430 extend from the copper member 350. Integrated circuit devices, shown generally 434, are mounted in the assembly along with other electrical components, shown generally as 436, and are electrically connected to each other and to the elongated conductive terminals 350 in a correct circuit manner. Thus, the preprocessing electronic circuit is arranged around the periphery of the focusable optical system, and continued in the same body portion as the optical system, forward of the solid-state imaging device.

FIG. 9 and FIG. 10 illustrate yet another embodiment for practicing the invention. The adapter top member 502 is shown attached to the body, shown generally as 500. The top member 502 includes a bayonet-type swivel which enables the endoscope camera to be attached to an endoscope having a bayonet receiving means. The remaining portion of the body 500 and its contents are generally of the construction discussed hereinbefore.

The descriptions and illustrations herein show a cable as the conducting or transmission means. However, the conducting means or transmitting means may be a radio frequency telemetering system having an appropriate power source, transmitting means and receiving means. Such a system would eliminate the need of a cable.

The endoscope conveying the optical image to the video camera could be fabricated such that the end of the endoscope could be directly affixed to or operatively adjacent to the surface of the solid-state imaging device inside the body of the camera. An alternative position of the end of the endoscope would be to locate the end thereof at the outside end of the adapter at the point of a coupling plane between the endoscope and adapter or, if so designed, spaced from the end of the adapter.

Also the optical system can have a folded optic path having a single or multiple prism or include some other similar type of optical deflecting or splitting means located along the optical path. Thus, the embodiment of FIG. 7 is merely exemplary and one configuration of the optical path.

While this invention has been explained with reference to the structure and method disclosure herein, it is not confined to the details as set forth, and this description and the following claims are intended to cover any modifications or changes that may come within the scope of the claims.

What is claimed is:

1. A video camera for use in medical surgical procedures in conjunction with an endoscope which produces an optical image comprising:

an optical system for receiving and optically processing an optical image from an endoscope;

a solid-state sensor-converter operatively positioned to receive the optical image after it has passed through the optical system and for converting the optical image to unprocessed video signals;

video electronic preprocessing circuit means adjacent the optical system and electronically connected to receive the output of the sensor-converter and mechanically mounted around the optical system;

means for transmitting preprocessing output signals of the video electronic preprocessing circuit means to a remote location to a video output circuit; and soakable enclosure means surrounding the optical system, the solid-state sensor-converter and the video electronic preprocessing circuit means and including means for permitting input of the optical image into the optical system and means for permitting transmission of the preprocessed output signals.

2. An integrated video camera for an endoscope which produces an optical image comprising:
   means defining an optical path for receiving at one end thereof the optical image from an endoscope and for optically passing said optical image along said optical path;
   means including a solid-state imaging means positioned along said optical path for receiving the optical image passed by said optical image passing means for converting the received optical image to video signals;
   video signal driving means located between said one end of the means defining said optical path and said solid-state imaging means and positioned relative to said optical path in a manner so as to permit the optical image to pass along said optical path onto said solid-state imaging means, said video signal driving means including means operatively connected to said solid-state imaging means for driving an external output means with said video signals; and
   soakable enclosure means surrounding the optical path defining means, the solid-state imaging means and the video driving means and including means for maintaining the same in operative relationship.

3. The apparatus of claim 2 further comprising means for attaching the video camera to an endoscope to receive the optical image from the endoscope.

4. An integrated video camera for an endoscope which produces an optical image comprising:
   means defining an optical path for receiving at one end thereof an optical image from an endoscope and for optically passing said optical image along said optical path;
   means including a solid-state imaging means positioned along said optical path for receiving the optical image passed by said optical image passing means for converting the received optical image to video signals; and
   video signal driving means located between said one end of the means defining said optical path and said solid-state imaging means and positioned relative to said optical path in a manner so as to permit the optical image to pass along said optical path onto said solid-state imaging means, said video signal driving means including means operatively connected to said solid-state imaging means for driving an external output means with said video signals.

5. The apparatus of claim 4 further comprising means for attaching the video camera to an endoscope to receive the optical image from the endoscope.

6. A highly compact video camera for use in medical and surgical procedures in conjunction with an endoscope which produces an optical image comprising:
   a body having an optically apertured front end portion and elongated sidewalls defining a cavity extending from the front end portion to a rear end portion;
   an optical system mounted inside the cavity having an optical axis operatively aligned with the aperture for receiving and optically processing the optical image transmitted through the aperture;
   sensor-converter means operatively placed in the cavity to receive the optical image processed through the optical system for converting the optical image to unprocessed video electronic signals;
   video electronic preprocessing circuit means in the cavity extending between the front and rear portions thereof and around the outside of the optical system; and
   means for electronically connecting the sensor-converter and the video electronic preprocessing circuit means to each other and to external means for providing signals from the video camera.

7. The video camera of claim 6 wherein the body comprising:
   a forward body portion defining a cavity in which is contained the optical system and the video electronic preprocessing cirucit means; and
   a rearward body portion in which is contained the sensor-converter.

8. The video camera of claim 6 wherein the video electronic preprocessing circuit means comprises:
   a circuit wiring containing a substrate at least partially surrounding the optical system and having circuit elements mounted on said substrate.

9. The video camera of claim 8 wherein the substrate extends around the optical system and has integrated circuit elements mounted on the substrate.

* * * * *